United States Patent
Bourgeois et al.

(10) Patent No.: US 6,369,127 B1
(45) Date of Patent: Apr. 9, 2002

(54) MATERIAL BASED ON SILICON, IN PARTICULAR FOR DENTAL IMPRESSION AND METHOD FOR MAKING SUCH MATERIAL

(75) Inventors: Daniel Bourgeois, Saint Genis Laval; Patrick Chauvet, Saint Quentin sur Isere, both of (FR)

(73) Assignee: Madrigal Finances (FR)

( * ) Notice: Subject to any disclaimer, the term of this patent is extended or adjusted under 35 U.S.C. 154(b) by 0 days.

(21) Appl. No.: 09/509,068

(22) PCT Filed: Sep. 23, 1998

(86) PCT No.: PCT/FR98/02044

§ 371 Date: Apr. 26, 2000

§ 102(e) Date: Apr. 26, 2000

(87) PCT Pub. No.: WO99/15132

PCT Pub. Date: Apr. 1, 1999

(30) Foreign Application Priority Data

Sep. 23, 1997 (FR) ............................................. 97 12044

(51) Int. Cl.[7] .................................................. A61K 6/10
(52) U.S. Cl. .................... 523/109; 424/78.07; 524/722; 524/723; 524/724
(58) Field of Search ...................... 523/109; 424/78.07; 524/724, 722, 723

(56) References Cited

U.S. PATENT DOCUMENTS 5,357,636 A * 10/1994 Dresdner et al. ............... 2/167
5,624,636 A    4/1997 Schwartz .................... 424/661

FOREIGN PATENT DOCUMENTS

| DE | 3423567 | 1/1986 |
| EP | 0 300309 | 1/1989 |
| EP | 0361301 | 4/1990 |
| FR | 2677013 | 12/1992 |

* cited by examiner

Primary Examiner—Peter Szekely
(74) Attorney, Agent, or Firm—Wall Marjama & Bilinski LLP

(57) ABSTRACT

A dispersion for making impression which are capable of gradually releasing antiseptic agent to the surface. The dispersion includes a silicone, a hydrophobic antiseptic agent which is incorporated into the silicone, with the concentration of hydrophobic agent in the dispersion being in the range of about 0.1% to 1% by weight of the total weight of the dispersion. The hydrophobic antiseptic agent is a mixture which includes a chelating agent, a phospholipid membrane attacking agent, and either a virus nucleocapsid attacking agent or a bacteria receptor site attacking agent.

22 Claims, No Drawings

MATERIAL BASED ON SILICON, IN PARTICULAR FOR DENTAL IMPRESSION AND METHOD FOR MAKING SUCH MATERIAL

BACKGROUND OF THE INVENTION

The invention relates to a novel silicone-based material. It applies more particularly, but without limitation, to a novel material for dental impression.

It also relates to a method of producing this material.

Many materials are currently used for the production of dental impressions and more particularly materials based on silicone or alginate.

The invention relates particularly to silicone-based materials. In a known manner, silicones are obtained by the crosslinking of a "base" of the organochlorosilane type, the crosslinking being initiated by a catalyst. The silicones obtained are either polycondensed silicones or silicones resulting from a polyaddition reaction.

In practice, silicones exist in the form of a thick or fluid paste which is placed on the base of a metal impression tray whose shape adopts that of the dental arch.

The impression tray/material assembly is then placed in the mouth and manually applied onto the dental arch for a period of between one and four minutes, according to the structural characteristics of the material used.

The impression tray and the material are then removed from the mouth and then sent to the dental technician who will produce the final prosthesis.

Even if the period during which the impression material remains in the mouth is relatively short, it is nevertheless sufficient for the material to be covered with the saliva and blood present in the patient's mouth. A number of bacteria, microbes and the like are then likely to develop not only at the surface, but also in the impression, which requires disinfecting the material as soon as it is removed from the patient's mouth, this being in order to observe basic rules of hygiene not only in relation to the dentist but also in relation to the dental technician. In addition, the patient is also concerned since it appears that often the prosthesis travels between the dental technician and the dentist in the same box as that in which the original impression tray existed.

As a method of disinfection, it is proposed in the document U.S. Pat. No. 5,624,636 to soak the dental impression in a hypochlorite bath for a period of between 1 and 5 minutes. A very relative efficacy of this type of treatment is observed since only a surface treatment is obtained.

To disinfect not only the surface but also the mass of the impression, it has been proposed in the document EP-A-0 361,301 to incorporate instead of the water necessary for the preparation of an alginate impression, an aqueous and microbicidal solution containing quaternary ammonium salts and a diguanidine compound, of specific formulae.

Even if this antiseptic is effective, it can only be introduced into a hydrophilic impression material, such as alginate, but is not in any case compatible with a hydrophobic material such as silicone. In addition, size stability problems are encountered as well as chemical and physical stability problems.

In other words, none of the solutions proposed up until now makes it possible to effectively disinfect the surface and the inside of a silicone-based impression since the treatment by the external route remains only slightly effective and the treatment by the internal route is effected using hydrophilic antiseptic agents, which cannot therefore be incorporated into hydrophobic materials.

SUMMARY OF THE INVENTION

The problem which the invention proposes to solve is therefore to provide a silicone-based dental impression material which is capable of being effectively disinfected.

To do this, the invention provides a silicone-based dental impression material comprising a hydrophobic antiseptic agent incorporated into the mass of the silicone and which can be gradually released up to the surface of the impression.

In other words, the invention consists in having incorporated an antiseptic agent which is compatible with silicone, and therefore hydrophobic, and which has the capacity to be released over time, developing a specific action, namely the gradual ionic release, allowing the disinfection both of the mass and the surface of the impression. The antiseptic agent therefore acts by an innovative process of self-disinfection of the silicone.

DESCRIPTION OF THE INVENTION

According to a first characteristic of the invention, the antiseptic agent comprises a chelating agent, an agent which is active on the phospholipid membranes of bacteria or viruses, and an agent which is active on the nucleocapsids of viruses or on any bacteria receptor site.

As chelating agent, ethylenediaminetetraacetic acid is advantageously used.

Moreover, the agent which is active on the phospholipid membranes of bacteria or viruses is a quaternary ammonium salt, in particular benzalkonium chloride.

As regards the agent which is active on the nucleocapsids of viruses or on any bacteria receptor site, sodium tosylchloramide or one of its chlorinated analogs is preferably used.

In other words, the antiseptic agent acts within the mass of the impression, gradually releasing the active chlorine ions derived from the benzalkonium chloride and those derived from the sodium tosylchloramide up to the surface of the impression. Thus by virtue of the internal and external action of the antiseptic agent, an impression free of any infectious microbes, viruses or bacteria is obtained in particular by virtue of the attachment of the chlorine atoms to the bacteria and virus receptor sites.

According to a preferred embodiment, the antiseptic agent comprises by mass:
- between 8 and 80% of ethylenediamine-tetraacetic acid;
- between 2 and 20% of benzalkonium chloride;
- between 1 and 20% of sodium tosylchloramide or one of its chlorinated analogs.

To promote galenic homogenization of the antiseptic preparation, the latter comprises a double amino acid, in particular aspartame.

To obtain an additional antiinflammatory and cicatrizing effect, the antiseptic agent comprises allantoin.

As sweetener and isotonicity adjuvant, the antiseptic agent comprises a natural flavoring and sorbitol.

To obtain a material free of any bacteria, microbes, viruses and the like, the proportion of antiseptic agent in said material is between 0.1 and 1% by mass.

For a value less than 0.1%, the proportion of antiseptic agent is not sufficient to obtain a disinfecting effect.

Likewise, a proportion of antiseptic agent greater than 1% does not improve the result obtained.

The invention also relates to the method of producing a silicone-based dental impression material, said silicone being obtained by the crosslinking of an organochlorosilane base, said crosslinking being initiated by a catalyst.

This method is characterized in that the antiseptic agent described above is incorporated into the organochlorosilane base, and then said organochlorosilane base is mixed with the catalyst in order to obtain the final material after crosslinking.

According to an essential characteristic of the method, the antiseptic agent comprises by mass:

from 8 to 80% of diethylenediaminetetraacetic acid;

from 2 to 10% of benzalkonium chloride;

from 1 to 10% of sodium tosylchloramide or one of its chlorinated analogs.

According to a preferred embodiment of the method, before incorporating the antiseptic agent into the organochlorosilane base:

the antiseptic agent is mixed beforehand with a silicone oil, the mixture obtained is then stirred and it is allowed to separate by settling, and finally, after filtration, the dispersion obtained is incorporated into the organochlorosilane base.

The invention and the advantages derived therefrom will emerge more clearly from the following exemplary embodiment.

280 grams of antiseptic agent comprising a chelating agent, an agent which is active on the phospholipid membranes of bacteria or viruses, and an agent which is active on the nucleocapsids of viruses or on any bacteria receptor site are prepared, whose mass (in grams) and nature are respectively:

| | |
|---|---|
| EDTA (ethylenediaminetetraacetic acid) | 80 g |
| Benzalkonium chloride | 38 g |
| Sodium tosylchloramide | 38 g |

The antiseptic agent comprises, in addition, by mass:

| | | |
|---|---|---|
| Homogenizing agent | aspartame | 15 g |
| Natural flavoring | mint | 8 g |
| Antiinflammatory agent | allantoin | 15 g |
| Isotonicity adjuvant | sorbitol | 86 g. |

The powder obtained is incorporated into 1 liter of silicone oil.

The mixture is stirred for one hour at a temperature of less than 37° C., preferably about 30° C.

The mixture obtained is allowed to separate by settling for 24 hours and then the product separated after settling is filtered. The powder obtained is then recovered.

0.3% by mass of this powder is then incorporated into 1000 grams of an organochlorosilane base.

The final silicone is then produced as is known by any person skilled in the art.

Thus, the base obtained is mixed with a catalyst in equal proportion, in the case where it is desired to obtain a polyaddition reaction silicone.

Nevertheless, the same operation may be carried out but with different proportions of base and catalyst in the case where it is desired to obtain a silicone resulting from a polycondensation.

The following trials were moreover carried out.

In a first instance, the characteristic of stability and structural conformity of the silicone-based material obtained according to the invention is checked.

It is thus observed that after storing for a period of 24 months, the material is perfectly preserved.

Moreover, it was observed that the crosslinking times for the silicone, that is to say for the base with the catalyst, proved to be identical in the presence or in the absence of the antiseptic agent.

The bacteriological properties of the impression material obtained were also checked.

Thus, three impressions were produced on different patients.

Each of the impressions was rinsed with running water for ten seconds, and then placed in culture in a vessel at 30° C. and for three days.

After 48 hours, no bacterial culture is observed at the surface of the impressions.

The invention therefore makes it possible to obtain a silicone-based dental impression material which exhibits no risk of infection both in the mass of silicone and at the surface thereof. It thus makes it possible to fulfill all the basic rules of hygiene in relation to the dentist, the dental technician and the patient.

Moreover, the silicone incorporating the antiseptic agent maintains its dimensional and structural stability over time.

In addition and as already stated, the invention is not limited to the field of dental impressions but applies to any technical sector which is likely to use silicone based materials which require disinfection.

What is claimed is:

1. A dispersion for making impressions, capable of gradually releasing antiseptic agent to the surface, comprising:

a silicone;

a hydrophobic antiseptic agent incorporated into said silicone, such that the concentration of said hydrophobic agent in said dispersion is between about 0.1% to 1% by weight of the total weight of the dispersion, said hydrophobic antiseptic agent being a mixture comprising a chelating agent, a phospholipid membrane attacking agent, and either a virus nucleocapsid attacking agent or a bacteria receptor site attacking agent.

2. The dispersion according to claim 1, wherein impressions made from said dispersions are self-disinfecting at the surface as well as in the body of said impressions.

3. The dispersion according to claim 1, wherein said chelating agent is ethylene diamine tetraacetic acid.

4. The dispersion according to claim 1, wherein said phospholipid membrane attacking agent is a quarternary ammonium salt.

5. The dispersion according to claim 4, wherein said quarternary ammonium salt is benzalkonium chloride.

6. The dispersion according to claim 1, wherein said virus nucleocapsid attacking agent or said bacteria receptor site attacking agent is selected from the group consisting of sodium tosylchloramide and its chlorinated analogs.

7. The dispersion according to claim 1, wherein said hydrophobic antiseptic agent comprises by weight:

between 8 and 80% ethylene diamine tetraacetic acid;

between 2 and 20% benzalkonium chloride;

and between 1 and 20% of sodium tosylchloramide or its chlorinated analog.

8. The dispersion according to claim 7, wherein said hydrophobic antiseptic agent further comprises a homogenizing agent selected from the group consisting of double amino acids.

9. The dispersion according to claim 8, wherein said double amino acid is aspartame.

10. The dispersion according to claim 7, wherein said hydrophobic antiseptic agent further comprises allantoin as an antiinflammatory and cicatrizing agent.

11. The dispersion according to claim 10, wherein said hydrophobic antiseptic agent further comprises sorbitol as a natural flavoring agent and an isotonicity adjuvant.

12. A method of obtaining a dispersion for making impressions, containing between about 0.1 to 1% by weight of a hydrophobic antiseptic agent and capable of gradually releasing said hydrophobic antiseptic agent to the surface, comprising the steps of:

(a) mixing the antiseptic agent with a silicone oil to obtain a mixture;

(b) stirring said mixture, allowing it to separate and followed by filtering to obtain a filtrate;

(c) mixing said filtrate with an organochlorosilane base;

(d) adding a catalyst to facilitate crosslinking of said organochlorosilane to obtain said dispersion capable of gradually releasing said hydrophobic antiseptic agent to the surface.

13. The dispersion obtained by the method of claim 12, wherein said antiseptic agent comprises, a chelating agent, a phospholipid membrane attacking agent, a virus nucleocapsid attacking agent, or a bacteria receptor site attacking agent.

14. The dispersion obtained by the method of claim 13, wherein said chelating agent is ethylenediaminetetraacetic acid.

15. The dispersion obtained by the method of claim 13, wherein said phospholipid membrane attacking agent is a quarternary ammonium salt.

16. The dispersion obtained by the method of claim 15, wherein said quarternary ammonium salt is benzalkonium chloride.

17. The dispersion obtained by the method of claim 13, wherein said virus nucleocapsid attacking agent or said bacteria receptor site attacking agent can be selected from sodium tosylchloramide and its chlorinated analogs.

18. The dispersion obtained by the method of claim 12, wherein said antiseptic agent comprises by weight:

between 8 and 80% ethylene diamine tetraacetic acid;

between 2 and 20% benzalkonium chloride;

and between 1 and 20% of sodium tosylchloramide or its chlorinated analog.

19. The dispersion obtained by the method of claim 13, wherein said antiseptic agent further comprises a homogenizing agent selected from the group consisting of double amino acids.

20. The dispersion obtained by the method of claim 19, wherein said double amino acids is aspartame.

21. The dispersion obtained by the method of claim 13, wherein said antiseptic agent further comprises allantoin as an antiinflammatory and cicatrizing agent.

22. The dispersion obtained by the method of claim 13, wherein said antiseptic agent further comprises sorbitol as a natural flavoring and an isotonicity adjuvant.

* * * * *